(12) United States Patent
Kolodji (10) Patent No.: US 11,247,176 B2
(45) Date of Patent: Feb. 15, 2022

(54) APPARATUS AND METHOD FOR DIRECT AIR CAPTURE OF CARBON DIOXIDE FROM THE ATMOSPHERE

(71) Applicant: Brian Kolodji, Bakersfield, CA (US)

(72) Inventor: Brian Kolodji, Bakersfield, CA (US)

(73) Assignee: Black Swan, LLC, Bakersfield, CA (US)

( * ) Notice: Subject to any disclaimer, the term of this patent is extended or adjusted under 35 U.S.C. 154(b) by 135 days.

(21) Appl. No.: 16/662,594

(22) Filed: Oct. 24, 2019

(65) Prior Publication Data

US 2021/0121826 A1    Apr. 29, 2021

(51) Int. Cl.
| | |
|---|---|
| *B01D 63/08* | (2006.01) |
| *B01D 53/22* | (2006.01) |
| *B01D 63/12* | (2006.01) |
| *C12M 1/00* | (2006.01) |

(Continued)

(52) U.S. Cl.
CPC .......... *B01D 63/08* (2013.01); *B01D 53/226* (2013.01); *B01D 53/227* (2013.01); *B01D 53/229* (2013.01); *B01D 63/12* (2013.01); *C12M 43/04* (2013.01); *E21B 43/164* (2013.01); *F23J 15/02* (2013.01); *B01D 2053/221* (2013.01); *B01D 2313/12* (2013.01); *B01D 2313/24* (2013.01); *B01D 2317/04* (2013.01); *F25J 2215/40* (2013.01)

(58) Field of Classification Search
None
See application file for complete search history.

(56) References Cited

U.S. PATENT DOCUMENTS

| | | |
|---|---|---|
| 4,073,089 A | 2/1978 | Maginnes et al. |
| 5,682,709 A | 11/1997 | Erickson |
| 6,108,967 A | 8/2000 | Erickson |

(Continued)

OTHER PUBLICATIONS

C. Maidana et al., Reduction of Fuel Consumption and Emissions of a Gas Turbine by Using of Oxygen-Enriched Combustion, 2nd Oxyfuel Combustion Conference.

(Continued)

*Primary Examiner* — Jason M Greene
(74) *Attorney, Agent, or Firm* — James M. Duncan; Scanlon Duncan LLP (57) ABSTRACT

An apparatus utilizes a membrane unit to capture components from atmospheric air, including carbon dioxide, enriches the carbon dioxide concentration, and delivers the enriched concentration of carbon dioxide to a sequestering facility. The membrane is configured such that as a first gas containing oxygen, nitrogen and carbon dioxide is drawn through the membrane, a permeate stream is formed where the permeate stream has an oxygen concentration and a carbon dioxide concentration higher than in the first gas and a nitrogen concentration lower than in the first gas. A permeate conduit, having a vacuum applied to it by a vacuum generating device receives the permeate stream and a delivery conduit delivers at least a portion of the enriched carbon dioxide to a sequestering facility. The apparatus may comprise a component of a system where the system may have a flue gas generator and/or a secondary enrichment system disposed between the vacuum generating device and the sequestering facility.

18 Claims, 11 Drawing Sheets

(51) Int. Cl.
*F23J 15/02* (2006.01)
*E21B 43/16* (2006.01)

(56) References Cited

U.S. PATENT DOCUMENTS

| | | | |
|---|---|---|---|
| 6,237,284 B1 | 5/2001 | Erickson | |
| 7,842,264 B2 | 11/2010 | Cooper et al. | |
| 8,137,527 B1* | 3/2012 | Woods | B01D 53/62 |
| | | | 205/555 |
| 8,197,857 B2 | 6/2012 | Dressler et al. | |
| 8,252,091 B2 | 8/2012 | Anand et al. | |
| 8,595,020 B2 | 11/2013 | Marino | |
| 8,852,319 B2 | 10/2014 | Wijmans et al. | |
| 8,889,400 B2 | 11/2014 | Martin et al. | |
| 9,266,057 B1 | 2/2016 | Jones | |
| 9,433,887 B2 | 9/2016 | Wijmans et al. | |
| 9,433,896 B2 | 9/2016 | Eisenberger | |
| 9,514,493 B2 | 12/2016 | Marino | |
| 2010/0205960 A1 | 8/2010 | McBride et al. | |
| 2011/0195473 A1 | 8/2011 | Wilhelm | |
| 2011/0260112 A1* | 10/2011 | Wijmans | B01D 53/22 |
| | | | 252/372 |
| 2013/0263734 A1* | 10/2013 | Wynn | B01D 53/228 |
| | | | 95/54 |
| 2018/0067091 A1* | 3/2018 | Burkhalter | A61L 2/04 |
| 2019/0321787 A1* | 10/2019 | Sivaniah | B01D 53/228 |
| 2020/0061529 A1* | 2/2020 | Zhu | B01D 53/22 |
| 2021/0060483 A1* | 3/2021 | Lackner | B01D 53/227 |

OTHER PUBLICATIONS

B.A. Kimball et al. Effects of Increasing Atmospheric CO2 on Vegetation printed in CO2 and Biosphere by J. Rozema et al. at p. 65, Kluwer Academic Publishers, 1993.

T. Brinkman, Theoretical and Experimental Investigations of Flat Sheet Membrane Module Types for High Capacity Gas Separation Applications, Chemie Ingenie Technik, vol. 85, Issue 8, pp. 1210-1220, May 17, 2013.

B. A. Kimball et al, Seventeen Years of Carbon Dioxide Enrichment of Sour Orange Trees: Final Results, Global Change Biology (2007) 13, 2171-2183.

T.C. Merkel et al, Power Plant Post-Combustion Carbon Dioxide Capture: An Opportunity for Membranes, Journal of Membrane Science 359 (2010) 126-139.

* cited by examiner

APPARATUS AND METHOD FOR DIRECT AIR CAPTURE OF CARBON DIOXIDE FROM THE ATMOSPHERE

BACKGROUND OF THE INVENTION

This invention relates to direct capture of carbon dioxide from the atmosphere utilizing membranes operating under vacuum, enriching the carbon dioxide concentration and forwarding the enriched carbon dioxide to a sequestration facility. Embodiments of the present invention may be utilized to reduce the overall concentration of carbon dioxide in the atmosphere. The term "sequestration facility" is defined herein as anyone of a variety of mechanisms which sequester the carbon dioxide thereby preventing immediate release back into the atmosphere. The term may include systems which utilize bio-sequestration, such as orchards, crops, forests, and other photosynthetic organisms which either convert carbon dioxide utilizing photosynthesis or store the carbon dioxide in the organism. The sequestration facility may also include manufacturing processes which utilize carbon dioxide. The sequestration facility may also include a system which injects carbon dioxide into petroleum reservoirs for purposes of enhanced oil recovery such as miscible flooding.

This application further relates to the utilization of membranes under vacuum for providing an enriched oxygen stream to a flue gas generator thereby decreasing fuel consumption and reducing the output of flue gas emissions. The carbon dioxide concentration in the flue gas, as compared to a flue gas generator without oxygen enrichment of the air supply, is highly enriched and thus suitable for various commercial uses, which may include enhanced oil recovery operations, agricultural use, medical applications, and other known commercial applications.

It is known that carbon dioxide is a major contributor to global warming. Global warming is a result of increasing concentrations of greenhouse gases ("GHG") in the atmosphere. Among the primary greenhouse gases are water vapor, carbon dioxide, methane, nitrous oxide, perfluorocarbons, hydrofluorocarbons, and sulfur hexafluoride. Of these, carbon dioxide is the primary anthropogenic (i.e., manmade) GHG, accounting for a substantial portion of the human contribution to the greenhouse effect in recent years.

There is an ongoing and critical need for additional mechanisms and methods for reducing consumption of non-renewable fuels and reducing atmospheric carbon dioxide.

SUMMARY OF THE INVENTION

Embodiments of the present invention exploit the unique property of membranes to economically achieve direct air capture of carbon dioxide from the atmosphere and separating carbon dioxide, oxygen, and water vapor from nitrogen and producing a permeate comprising enriched concentration of carbon dioxide, oxygen and water, and a reduced concentration of nitrogen. Instead of using processes which yield highly purified concentrations of carbon dioxide and oxygen at significant capital expense and significant operating costs, embodiments of the present invention utilize low pressure "leaf" membrane units to remove nitrogen from the atmospheric air and thereby mildly or moderately increasing the concentrations of the carbon dioxide and the oxygen in the permeate. The resulting permeate stream does not have to be highly purified to attain significant benefits.

Embodiments of the present invention may utilize membrane materials having properties similar to those of the cellulose acetate based sheet or spiral wound type membrane units used in the Separex™ membrane product as manufactured by Honeywell/UOP, or other polymeric based membrane products such as "plate and frame" type Polaris™ membranes as manufactured by MTR, Inc., or hollow fiber type membrane units such as Cynara™ membranes manufactured by Schlumberger, or PRISM™ membranes as manufactured by Air Products. However, these known membrane devices have significant supporting structure and require blowers or compressors for operation of the systems.

The use of the above listed membrane materials and products enrich the oxygen and carbon dioxide concentrations of a gas stream processed through the membrane units. Carbon dioxide and oxygen pass or permeate more rapidly through the membrane relative to nitrogen, thereby forming a permeate stream which is more concentrated or enriched in oxygen and carbon dioxide than the "feed" stream. It is noted that the term "feed" is used somewhat loosely for purposes of this disclosure and does not refer to a stream delivered to the membrane via an intake or similar structure. With embodiments of the presently disclosed leaf membranes, a "feed" side of the membrane (which may also be referred to as the "outer side" but should not be thereby limited to an exterior position) is exposed to a gas, i.e., air, which is brought into the membrane unit by a vacuum applied to the membrane unit. Gas components which pass relatively slowly through the membrane in comparison to oxygen, carbon dioxide and water, such as nitrogen, remain mostly on the same side of the membrane as the "feed" stream and disbursed into the atmosphere.

In one embodiment of the invention, a flue gas generator may be disposed between the membrane unit and the sequestration facility. The combustion processes utilized in flue gas generators conventionally use atmospheric air to produce a flue gas that contains carbon dioxide concentrations well above that found in atmospheric air. As indicated above, the permeate stream generated from the disclosed membrane units has higher concentrations of carbon dioxide and oxygen than atmospheric air. When the permeate stream is introduced into a combustion process in place of atmospheric air, the result is a flue gas having a carbon dioxide concentration well above that from using conventional combustion air. This carbon dioxide enriched flue gas may then be utilized in the sequestration facilities discussed above. In some embodiments of the invention the flue gas generator may be pressurized thereby eliminating the need for downstream pressurization.

Embodiments of the present invention may also comprise a secondary (or tertiary) enrichment system which utilizes the permeate from a first stage membrane unit as a feed for secondary membrane units contained within enclosures such as conduit or piping or as feed for a cryogenic oxygen enrichment system.

A unique vacuum system may be utilized for application of vacuum to the membrane units. The disclosed bellows system is relatively simple and requires low power input to generate the vacuum necessary to process a feed gas through the disclosed leaf membranes.

A method of direct air capture of carbon dioxide utilizing membrane members under vacuum is also disclosed.

DETAILED DESCRIPTION OF THE EMBODIMENTS

Figure 1:
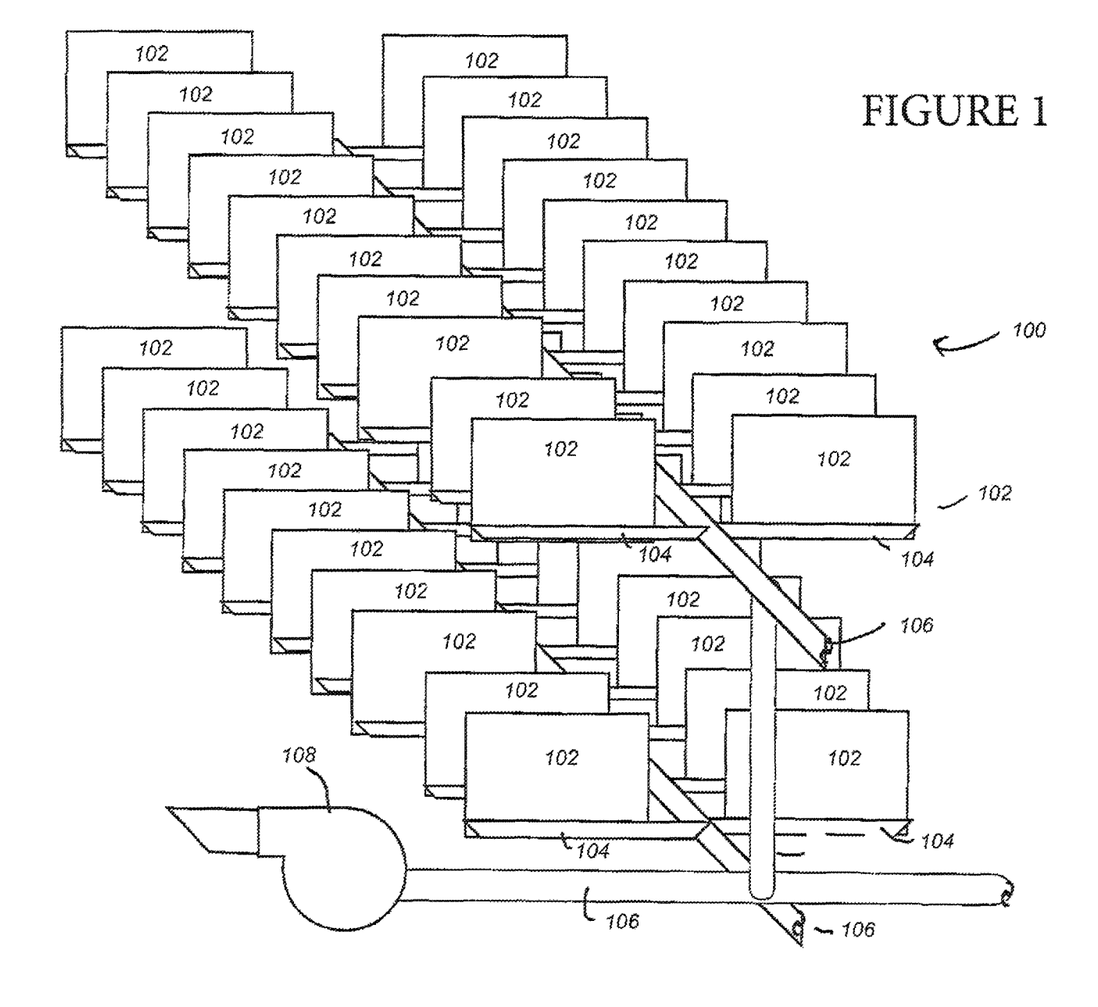
FIG. 1 depicts a configuration for a bank or array of leaf membrane units which may be utilized for direct air capture of atmospheric air.

FIG. 1 depicts a configuration for an array or bank 100 formed by a plurality of leaf membrane units 102 for direct air capture of components of atmospheric air, specifically oxygen, nitrogen, water vapor, and, most importantly, carbon dioxide. It is to be appreciated that a plurality of banks 100 as depicted in FIG. 1 may be deployed to increase the direct air capture of carbon dioxide. Once captured, leaf membrane units 102 separate oxygen, carbon dioxide and water from nitrogen, forming a permeate comprising enriched concentrations of oxygen, carbon dioxide and water, but a depleted level of nitrogen. The separated nitrogen simply returns to the atmosphere while the permeate, flows into delivery conduit 104 and into headers 106. A vacuum generating device 108 applies a vacuum to the leaf membrane units 102 of bank 100. Vacuum generating device applies a strong vacuum to the leaf membrane units. Among the acceptable vacuum generating devices 108 are blowers, liquid ring compressors, or the bellows vacuum system described below and schematically depicted in FIG. 11.

It is to be appreciated that multiple membrane banks 100 may be utilized to increase the capture of carbon dioxide from the atmosphere. Because the disclosed systems, including the membranes, the conduits, and the vacuum generating devices can be produced at relatively low cost, the only significant detriment in utilizing a substantial number of membrane banks 100 is the amount of area required for placement of the units.

Figure 2:
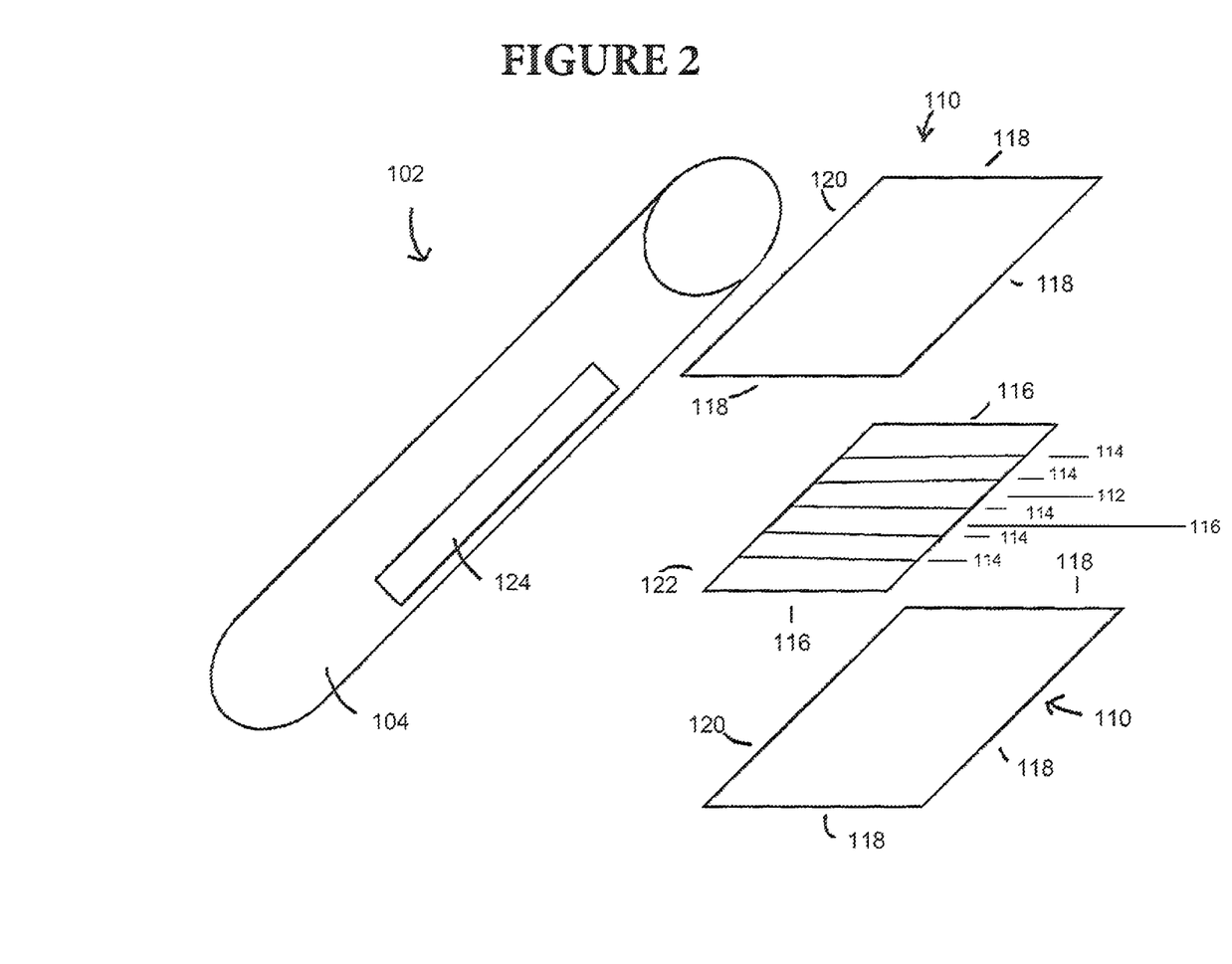
FIG. 2 depicts an exploded view of an embodiment of a leaf membrane unit which may be utilized for low pressure direct air capture of carbon dioxide.

FIG. 2 shows an exploded view of a leaf membrane unit 102 from the membrane bank 100. Leaf membrane unit 102 comprises surface membrane sheets 110 which are disposed on either side of barrier ribbed sheet 112. Each side of the barrier ribbed sheet 112 comprises a plurality or ribs 114. Barrier ribbed sheet 112 comprises edges 116 which are attached to corresponding edges of the sides 118 of each surface membrane sheet 110 which are in facing relation to each side the barrier ribbed sheet 112. Leaf membrane unit 102 takes neat (meaning ambient atmospheric) air allows oxygen, carbon dioxide and water to pass through surface membrane sheets 110, thereby producing a lower total volume of and significantly higher concentration in the permeate stream of oxygen, carbon dioxide and water, and significantly lower concentration of nitrogen. The elimination of most or all of the nitrogen than in the air results in a permeate stream of enriched concentrations of oxygen, carbon dioxide and water. The permeate flows into the respective envelopes created between the opposing faces of each surface membrane sheet 110 and the barrier ribbed sheet 112 defining, with respect only to the orientation shown in FIG. 2, an upper envelope and a lower envelope, with conjoined edges 116, 118 enclosing all but one side of the upper envelope and the lower envelope.

The permeate is directed by ribs 114 towards an open side of the upper envelope and an open side of the lower envelope at unattached edges 120 of the surface membrane sheets 110 and unattached edge 122 of the barrier ribbed sheet 112. The open side at unattached edges 120, 122 is inserted into slot 124 of permeate conduit 104.

Figure 3:
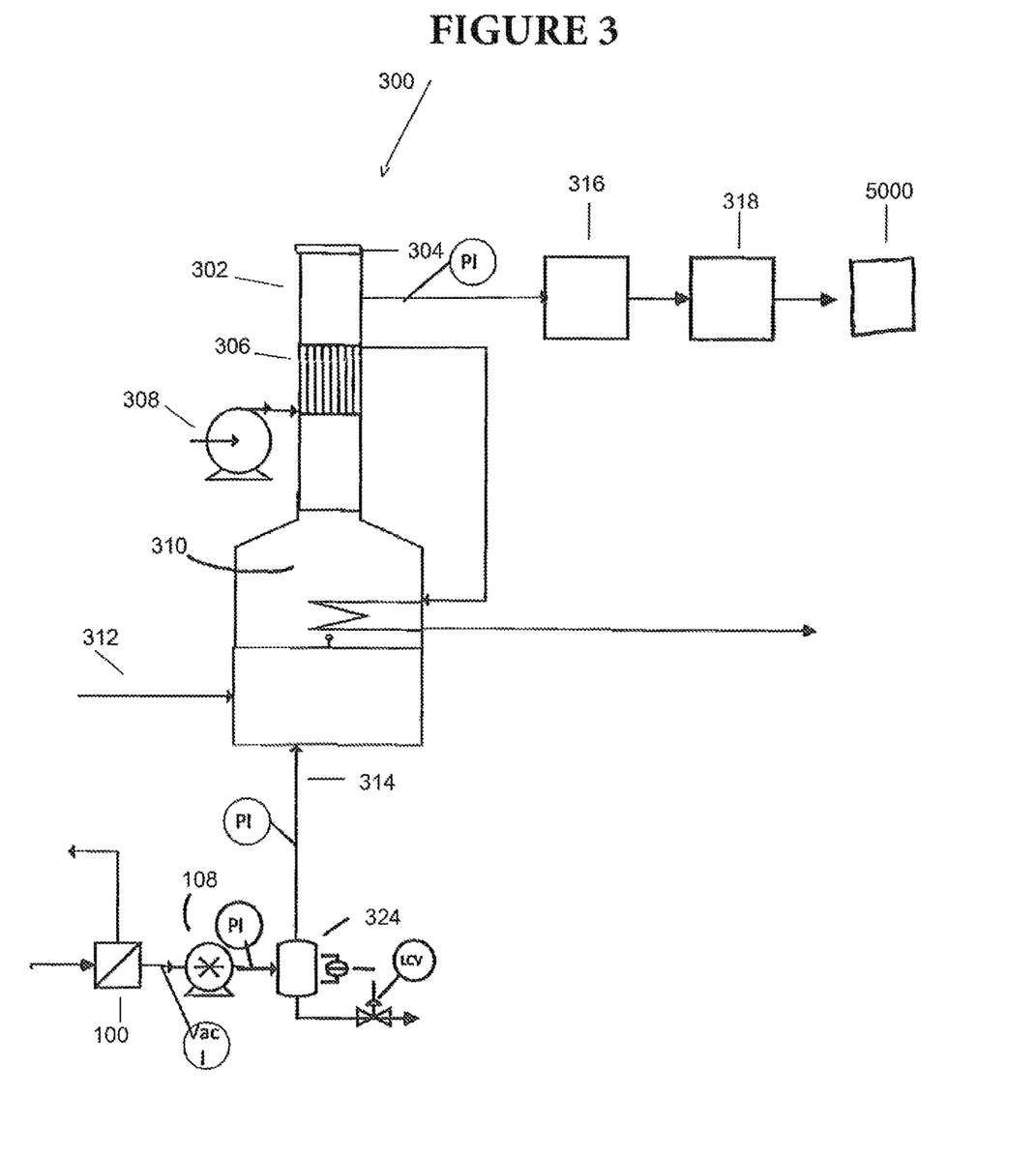
FIG. 3 shows a system which may utilize embodiments of leaf membranes for low pressure enrichment of a gas stream comprising oxygen and carbon dioxide flowing into a flue gas source.
Figure 4:
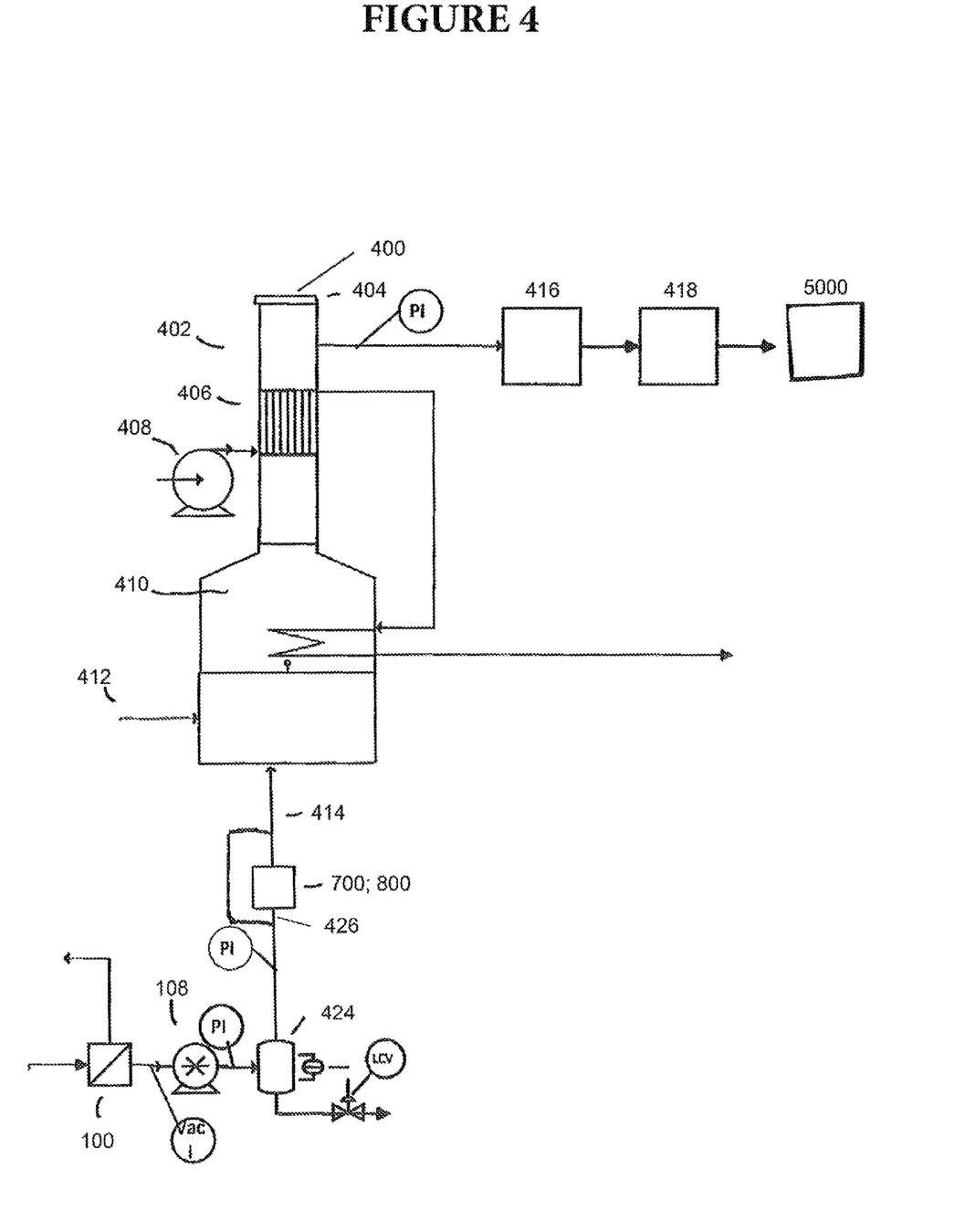
FIG. 4 depicts a system which may utilize embodiments of leaf membranes for low pressure enrichment and a separate system for secondary enrichment of a gas stream comprising oxygen and carbon dioxide flowing into a flue gas source.
Figure 5:
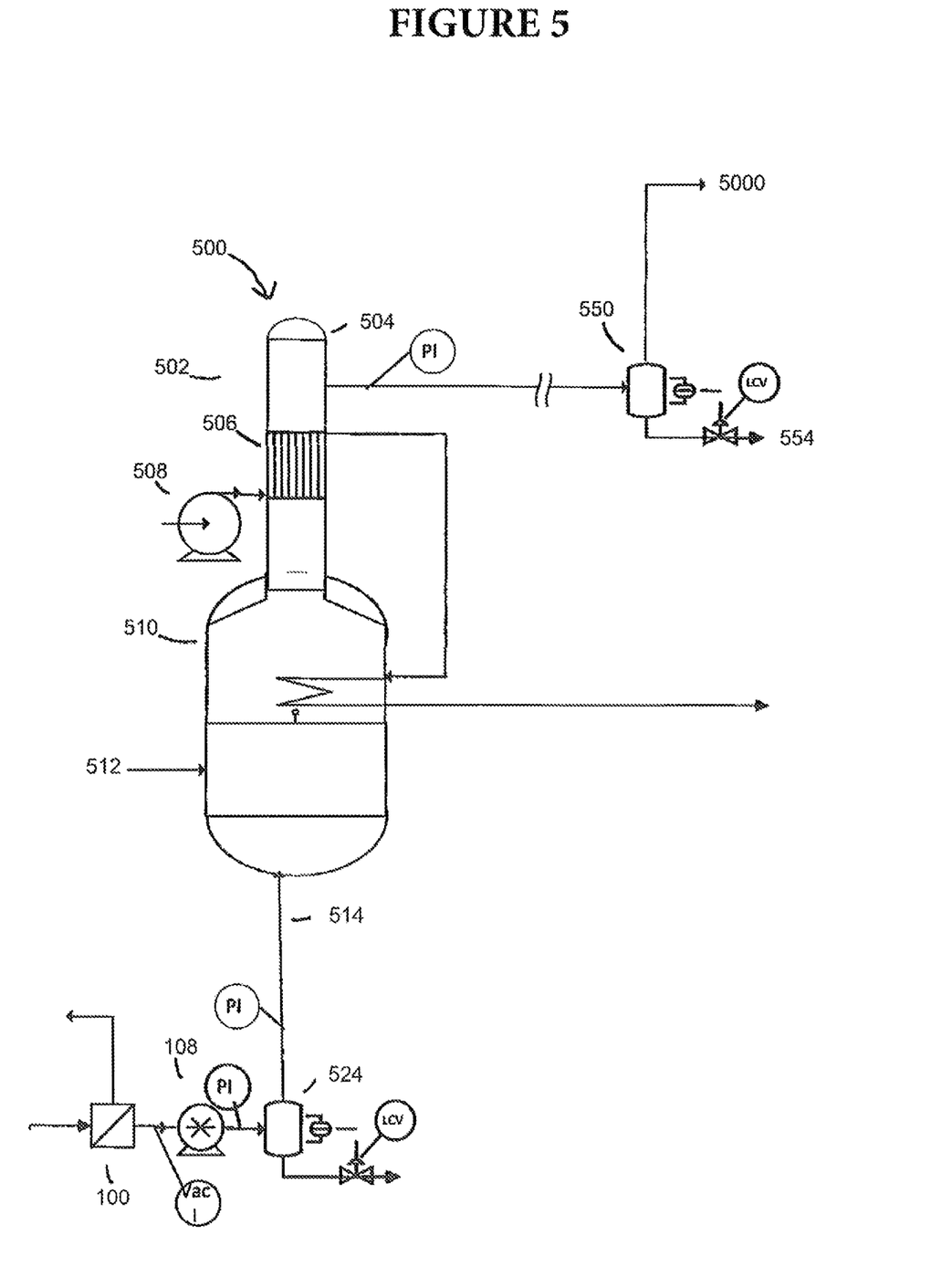
FIG. 5 depicts a system which may utilize embodiments of leaf membranes for low pressure enrichment of a gas stream comprising oxygen and carbon dioxide flowing into a pressurized flue gas source.
Figure 6:
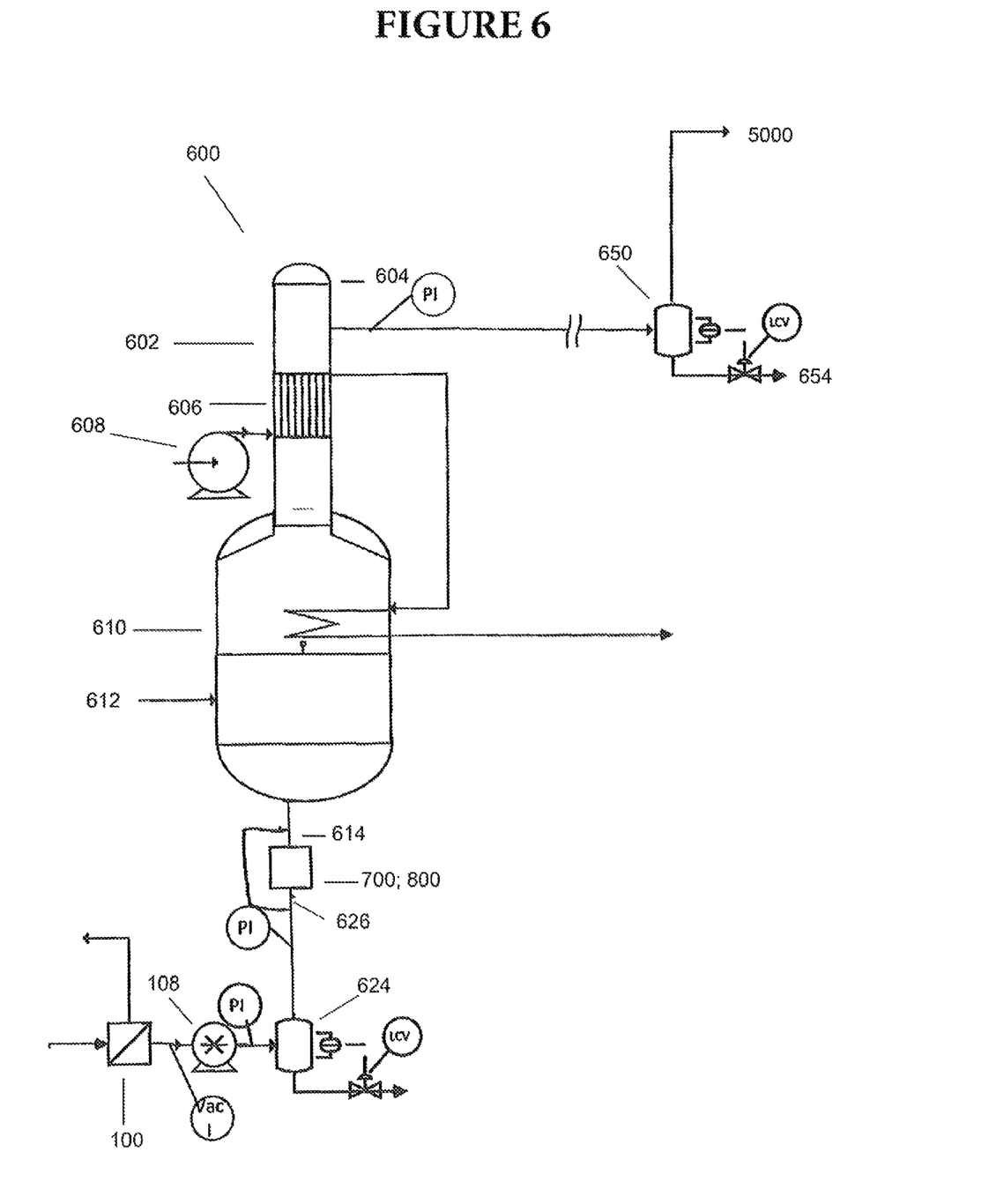
FIG. 6 depicts a system which may utilize embodiments of leaf membranes for lower pressure enrichment and a separate system for secondary enrichment of a gas stream comprising oxygen and carbon dioxide flowing into a pressurized flue gas source.

FIGS. 3-6 depict different generalized configurations of a flue gas generator 300, 400, 500, 600 which may be utilized in the various embodiments of the invention. FIG. 3 depicts a base embodiment 300 which utilizes a membrane bank 100 upstream of the flue gas generator 300. FIG. 4 depicts an alternative embodiment 400 which utilizes a membrane bank 100 but also includes structure for secondary enrichment of the permeate stream. FIG. 5 depicts an alternative embodiment 500 which utilizes membrane bank 100 but also utilizes a pressurized flue gas generator. FIG. 6 depicts an alternative embodiment 600 which utilizes a membrane bank 100, the structure for secondary enrichment of the permeate stream, and utilizes a pressurized flue gas generator.

For the base embodiment, flue gas generator 300 may have a stack 302 which may be capped with a closure device 304 at the tip. Flue gas generator 300 may have an economizer 306, which is a heat exchanger which saves on fuel gas by preheating boiler feed water from ambient temperature on the tube side up to approximately 200 degrees Fahrenheit, utilizing hot stack gas on the shell side, utilizing a boiler feed water pump 308. Fuel for the boiler 310 is delivered through fuel inlet 312. "Air" for the boiler 310 is delivered through air inlet 314, although the "air" provided through the inlet will comprise permeate provided by membrane bank 100. Discharge from flue gas generator 300, which may comprise an enriched concentration of carbon dioxide, may be delivered to a cooler 316 with the cooled gas dehydrated with liquids removal equipment (not shown) and then pressurized by a compressor or blower 318 for delivery to a sequestration facility 5000, which may include systems which utilize bio-sequestration, such as orchards, crops, forests, and other photosynthetic organisms which either convert carbon dioxide utilizing photosynthesis or store the carbon dioxide in the organism. The sequestration facility 5000 may also include manufacturing processes which utilize carbon dioxide. The sequestration facility 5000 may also include a system which injects carbon dioxide into petroleum reservoirs for purposes of enhanced oil recovery such as miscible flooding.

Figure 11:
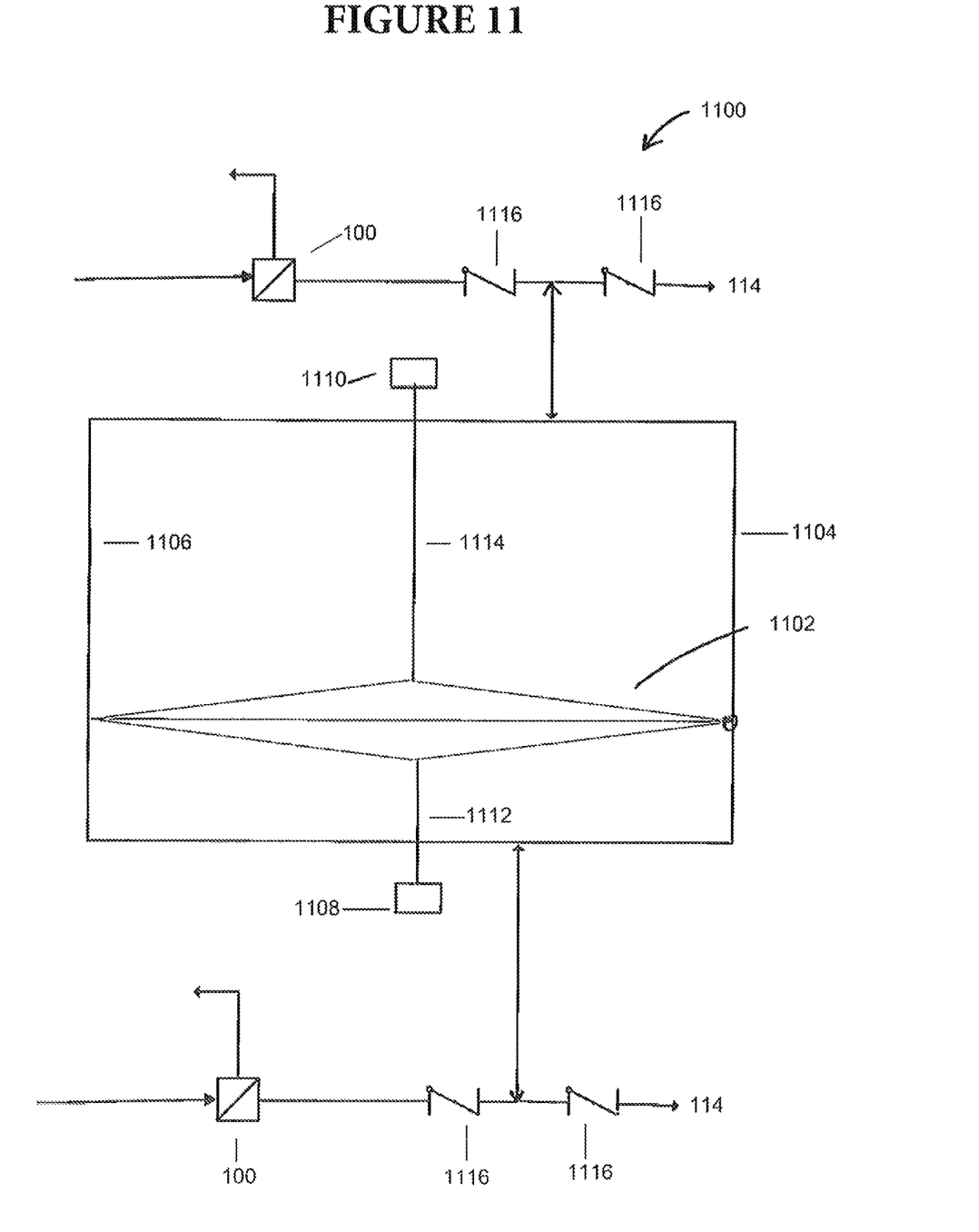
FIG. 11 schematically depicts an embodiment of a bellows vacuum system for alternatively applying vacuum to a permeate stream in a low-pressure membrane and for generating pressure to deliver the permeate for further processing.

Air provided to the boiler 310 first passes through membrane bank 100. Membrane bank 100 utilizes a vacuum generating device 108 to draw ambient or atmospheric air into contact with the individual leaf membrane units 102, and to pull the permeate through each membrane. The vacuum generating device 108 may be a blower or a liquid ring compressor, although both types of devices require liquid separation. Alternatively, a bellows vacuum device 1100 as schematically depicted in FIG. 11 may be utilized. Vacuum generating device 108 discharges a permeate stream which, after being dehydrated as necessary by separator 324, is delivered to air inlet 114.

The bellows vacuum device 1100 uses less energy than a blower or a liquid ring compressor. The bellows vacuum device may be fabricated from a large enclosure, such as a tank. It is to be noted that because of the low speeds at which the bellows vacuum system operates, and the lubrication to be provided between the cylinder walls and piston, that little or no heat will be generated at the discharge of the device.

As shown in FIG. 11, double-acting piston 1102 is set within a large cylinder 1104. Piston 1102 may have graphite rings and/or the cylinder walls 1106 may comprise graphite. Actuation devices 1108, 1110 respectively utilize connectors 1112, 1114 to actuate piston 1102 in either direction within the cylinder 1104. It is to be appreciated that large cylinder 1104 need not be a pressure vessel and that actuation devices 1108, 1110 may be small winches driven by small motors and connectors 1112, 1114 may be light rods or small diameter cables. Double-acting piston 1102 may be diamond-shaped to provide additional structural integrity under vacuum conditions.

As indicated in FIG. 11, bellows vacuum device 1100 applies vacuum to membrane banks 100 on each upstroke (relative to the position of the oxygen enrichment membrane) of the piston 1102 within cylinder 1104, thereby causing permeate to be pulled into cylinder 1104. On the downstroke, with the action of check valves 1116, permeate is pushed out of cylinder 1104 and into air inlets 314, 414, 514, 614 and into the boilers 310, 410, 510, 610 of the respective flue gas generators 300, 400, 500, 600

For the alternative embodiment depicted in FIG. 4, flue gas generator 400 may have a stack 402 which may be capped with a closure device 404 at the tip. Flue gas generator 400 may have an economizer 406, which is a heat exchanger which saves on fuel gas by preheating boiler feed water from ambient temperature on the tube side up to approximately 200 degrees Fahrenheit, utilizing hot stack gas on the shell side, utilizing a boiler feed water pump 408. Fuel for the boiler 410 is delivered through fuel inlet 412. "Air" for the boiler 410 is delivered through air inlet 414, although the "air" provided through the inlet will have enriched concentrations of oxygen, carbon dioxide and water and a reduced concentration if nitrogen, as described below. Discharge from flue gas generator 400, which may comprise an enriched concentration of carbon dioxide, may be delivered to a cooler 416 with the cooled gas dehydrated with liquids removal equipment (not shown) and then pressurized by a compressor or blower 418 for delivery to a sequestration facility 5000.

Air provided to the boiler 410 first passes through membrane bank 100. Membrane bank 100 utilizes a vacuum-generating device 108 to draw ambient air into contact with the individual leaf membrane units 102 and pull the permeate through each individual membrane. As previously discussed, the vacuum generating device may be any of the various types described for the embodiment depicted in FIG. 3. Vacuum generating device 108 discharges a permeate stream which, after being dehydrated as necessary by separator 424 may be delivered to air inlet 414 and/or routed to inlet 426 to secondary enrichment mechanism 700, 800, embodiments of which are described in greater detail below and depicted, respectively, in FIGS. 7-8. Alternatively, the secondary enrichment mechanism may comprise a known cryogenic oxygen enrichment system.

For the alternative embodiment depicted in FIG. 5, flue gas generator 500 is pressurized. The flue gas generator 500 has a stack 502 which is capped with a closure device 504 at the tip. Flue gas generator 500 may have an economizer 506, which is a heat exchanger which saves on fuel gas by preheating boiler feed water from ambient temperature on the tube side up to approximately 200 degrees Fahrenheit, utilizing hot stack gas on the shell side, utilizing a boiler feed water pump 508. Fuel for the boiler 510 is delivered through fuel inlet 512. "Air" for the boiler 510 is delivered through air inlet 514, although the "air" provided through the inlet will have enriched concentrations of oxygen, carbon dioxide and water and a reduced concentration of nitrogen. Discharge from flue gas generator 500 is emitted at a pressure in excess of atmospheric pressure and therefore may have a highly enriched concentration of carbon dioxide. The discharge may be routed to separator 550, with enriched carbon dioxide discharged to sequestration facility 5000 and liquids discharged through outlet 554.

Air provided to the boiler 510 first passes through membrane bank 100. Membrane bank 100 utilizes a vacuum-generating device 108 to draw ambient air into contact with the individual leaf membrane units 102 and pull the permeate through each individual membrane. As previously discussed, the vacuum generating device may be any of the various types described for the embodiment depicted in FIG. 3. Vacuum generating device 108 discharges a permeate stream which, after being dehydrated as necessary by separator 524, is delivered to air inlet 514.

For the alternative embodiment depicted in FIG. 6, flue gas generator 600 is pressurized. The flue gas generator 600 has a stack 602 which is capped with a closure device 604 at the tip. Flue gas generator 600 may have an economizer 606, which is a heat exchanger which saves on fuel gas by preheating boiler feed water from ambient temperature on the tube side up to approximately 200 degrees Fahrenheit, utilizing hot stack gas on the shell side, utilizing a boiler feed water pump 608. Fuel for the boiler 610 is delivered through fuel inlet 612. "Air" for the boiler 610 is delivered through air inlet 614, although the "air" provided through the inlet will have enriched concentrations of oxygen, carbon dioxide and water. Discharge from flue gas generator 600 is emitted at a pressure in excess of atmospheric pressure and therefore may have a highly enriched concentration of carbon dioxide. The discharge may be routed to separator 650, with enriched carbon dioxide discharged to sequestration facility 5000 and liquids discharged through outlet 654.

Air provided to the boiler 610 first passes through membrane bank 100. Membrane bank 100 utilizes a vacuum-generating device 108 to draw ambient air into contact with the individual leaf membrane units 102 and pull the permeate through each individual membrane. As previously discussed, the vacuum generating device may be any of the various types described for the embodiment depicted in FIG.

3. Vacuum generating device 108 discharges a permeate stream which, after being dehydrated as necessary by separator 624 may be delivered to air inlet 614 and/or routed to inlet 626 to secondary enrichment mechanism 700, 800, embodiments of which are described in greater detail below and depicted, respectively, in FIGS. 7-8. Alternatively, the secondary enrichment mechanism may comprise a known cryogenic oxygen enrichment system.

Figure 7:
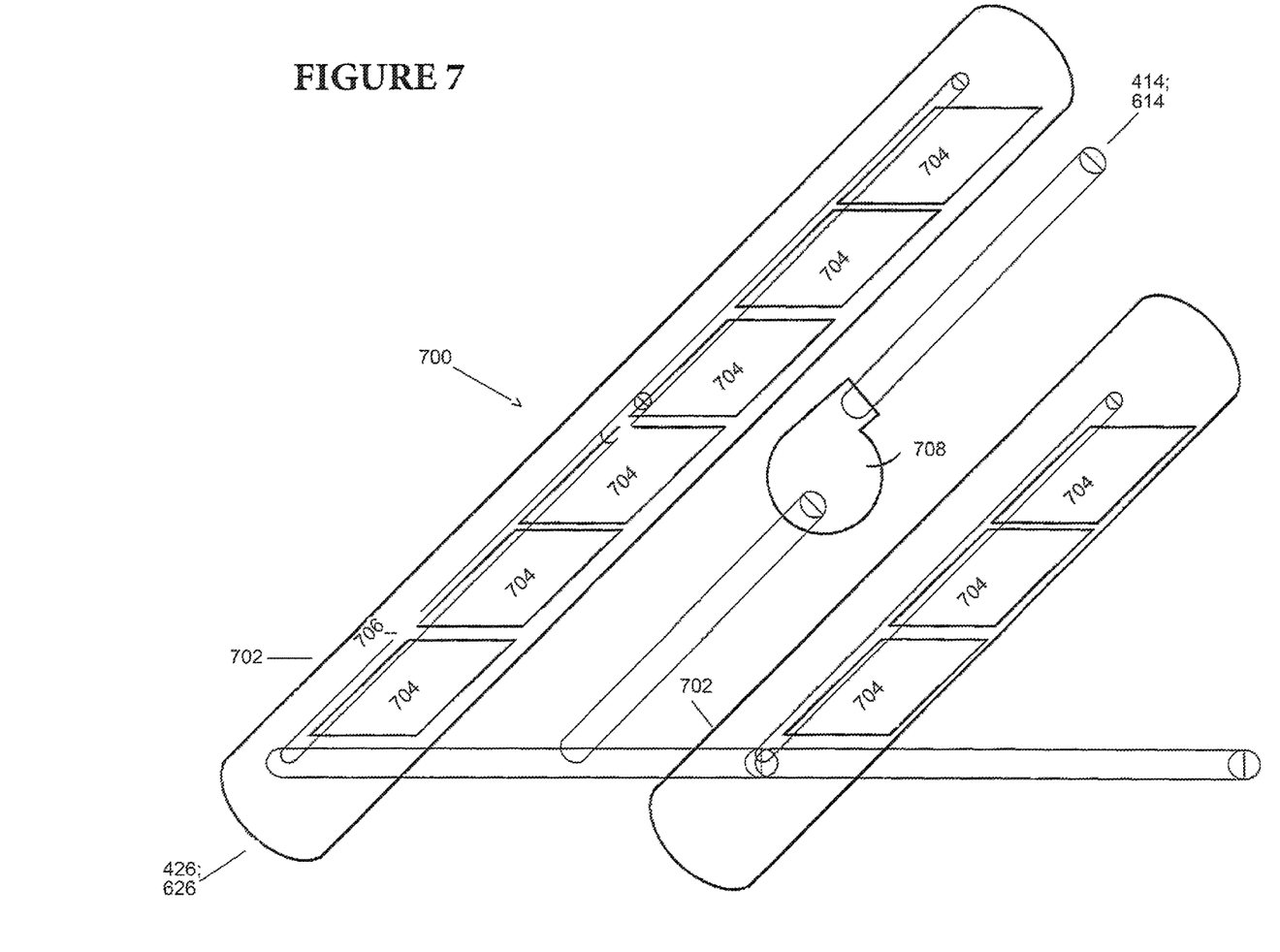
FIG. 7 depicts an embodiment of a configuration of membrane units mounted within enclosed conduits which may be utilized for secondary (and tertiary) enrichment of a permeate stream in embodiments of the invention.
Figure 8:
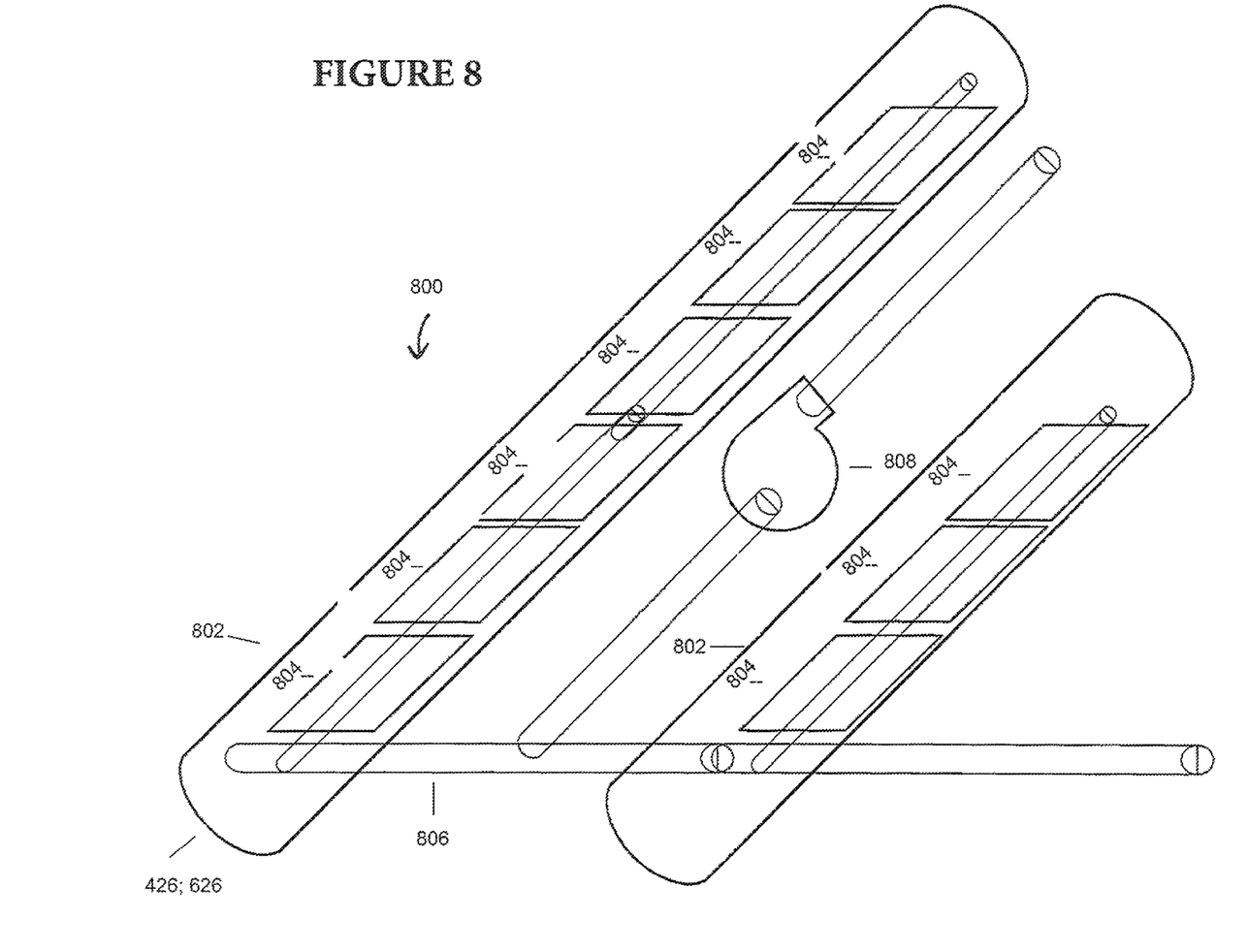
FIG. 8 depicts an alternative embodiment of a configuration of membrane units mounted within enclosed conduits which may be utilized for secondary (and tertiary) enrichment of a permeate stream in embodiments of the invention.

FIG. 7 depicts an embodiment of a secondary enrichment mechanism 700. Secondary oxygen enrichment mechanism 700 receives "feed" (i.e., permeate from membrane bank 100) through inlets 426, 626. The feed flows into enclosed conduit 702 where the feed encounters membrane units 704. In this embodiment of the secondary oxygen enrichment mechanism 700, the membrane units 704 may be the leaf membrane units 102 described above and depicted in FIG. 2. However, instead of being exposed to the atmosphere, the membrane units 704 of secondary enrichment mechanism 700 are entirely enclosed and the feed is provided under pressure, with a pressure differential created at headers 706 by blower 708, which delivers the permeate either to a tertiary enrichment mechanism, such as another membrane system as depicted in FIGS. 7, 8 and shown schematically in FIG. 10, or to air inlets 414, 614 for boilers 410, 610. Residue from the secondary enrichment mechanism 700 remains within enclosed conduit 702 and may be discharge through an outlet, not shown.

FIG. 8 depicts an embodiment of a secondary enrichment mechanism 800. Secondary enrichment mechanism 800 receives "feed" (i.e., permeate from membrane bank 100) through inlets 426, 626. The feed flows under pressure into enclosed conduit 802 where the feed encounters membrane units 804.

Figure 9:
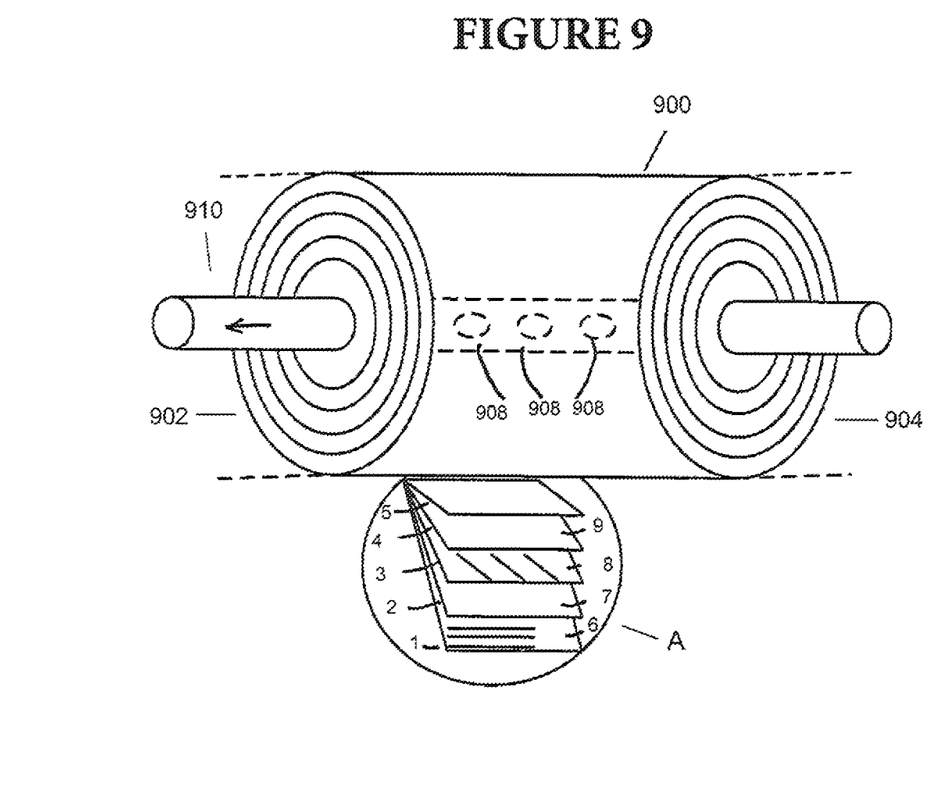
FIG. 9 depicts an embodiment of a membrane unit which may be utilized in a system as depicted in FIG. 8.

In this embodiment of the secondary enrichment mechanism 800, the membrane units 804 may be spiral wound membrane units 900 as depicted in FIG. 9, with the feed entering into the front face 902 of each unit and the residue stream leaving the rear face 904 of each unit. Spiral wound membrane unit 900 is fabricated from alternating sheets of membrane sheets and spacer sheets. An expanded detail of an unwound membrane unit is shown in detail A of FIG. 9, where the spiral membrane unit has the following elements: (1) a bottom feed/residue spacer 1; (2) a bottom membrane sheet 2; (3) a permeate spacer 3; (4) a top membrane sheet 4; (5) a top feed/residue spacer 5; (6) a bottom feed/residue channel 6; (7) a bottom feed permeate channel 7; (8) a top permeate channel 8; and (9) a top feed/residue channel 9. The membrane sheet layers 2, 4 are glued to the feed/residue spacers 1, 5 at the front edges only and glued to the permeate spacer 3 at the front and the side edges. The open ends of permeate channels 7, 8 are attached over perforations in the permeate collection pipe 908. The top feed/residue spacer 5 is longitudinally ribbed on the bottom of the spacer and the bottom feed/residue spacer 1 is longitudinally ribbed on the top of the spacer. Permeate spacer 3 is laterally ribbed on the top and bottom of the spacer.

Gas flows in a spiral pattern through the spiral wound membrane with the permeate received by permeate collection pipe 910. The ends of permeate collection pipe 910 may threaded so that the spiral wound membrane units may be attached in an end-to-end configuration for collection of the permeate. Permeate collection pipes 910 are connected to permeate collection header 806

The membrane units 904 for secondary enrichment mechanism 900 are entirely enclosed and the feed is provided under pressure, with a pressure differential created at permeate collection header 806 by blower 808, which delivers the permeate either to a tertiary enrichment mechanism, such as another membrane system as depicted in FIGS. 7, 8 or to air inlets 414, 614 for boilers 410, 610. Residue from the secondary enrichment mechanism 800 will remain within enclosed conduit 802 and may be discharge through an outlet, not shown.

Figure 10:
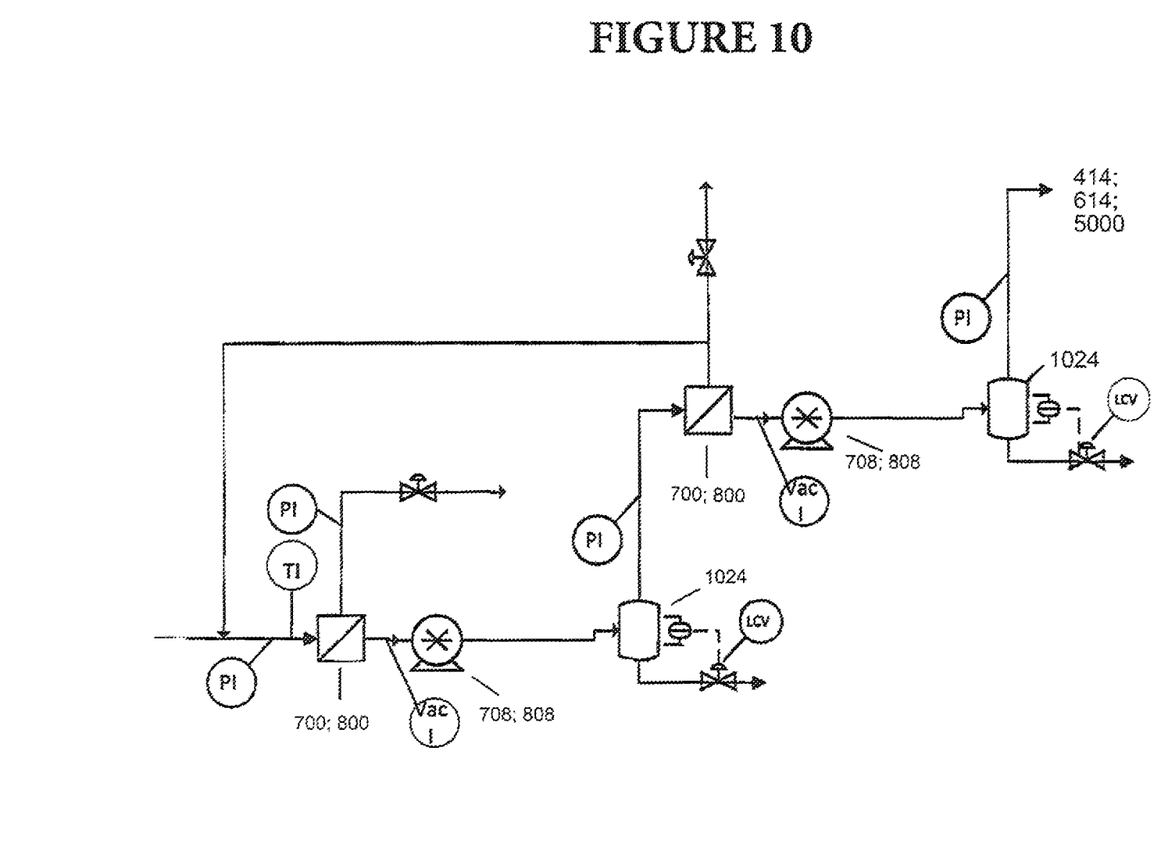
FIG. 10 depicts a piping configuration which may be utilized for a secondary and tertiary enrichment of a permeate stream.

FIG. 10 schematically depicts a configuration of a secondary and tertiary enrichment structures which may be utilized in embodiments of the invention. As indicated in the figures, vacuum-generating devices 708, 808, as described herein are required to pull the feed gas through the membranes of secondary enrichment mechanisms 700, 800 and pressurize the post membrane permeate to service destinations which may include sequestration facility 5000. For secondary enrichment mechanisms 700, 800 a strong vacuum blower 708, 808, usually a liquid ring compression device, is needed to pull the permeate through. Dehydration and liquid separation devices 1024 are required.

With the embodiments of the invention disclosed herein, the flue gas stream from the flue gas generator 300, 400, 500, 600 is reduced in volume and thus more economical to transport because ducts and permeate blower systems may be substantially reduced in size.

While the above is a description of various embodiments of the present invention, further modifications may be employed without departing from the spirit and scope of the present invention. Thus the scope of the invention should not be limited according to these factors, but according to the following appended claims.

What is claimed is:

1. An apparatus for direct air capture of components of atmospheric air comprising:

a membrane unit comprising an outer surface and an inner surface, wherein the membrane unit is configured such that as a first gas comprising a first concentration of nitrogen, a first concentration of oxygen, a first concentration of water, and a first concentration of carbon dioxide is drawn into the outer surface and passes through the membrane, a permeate stream exits the inner surface where the permeate stream comprises a second concentration of nitrogen, a second concentration of oxygen, a second concentration of water, and a second concentration of carbon dioxide wherein the second concentration of oxygen is greater than the first concentration of oxygen, the second concentration of water is greater than the first concentration of water, the second concentration of carbon dioxide is greater than the first concentration of carbon dioxide, and the second concentration of nitrogen is less than the first concentration of nitrogen;

a permeate collection device which collects the permeate stream;

a vacuum-generating device which applies a vacuum to the membrane unit; and a delivery conduit which conducts at least a portion of the permeate stream to a flue gas generator wherein the flue gas generator is disposed between the vacuum generating device and a sequestering facility.

2. The apparatus of claim 1 wherein the sequestering facility comprises a plurality of photosynthetic organisms.

3. The apparatus of claim 1 wherein the sequestering facility comprises an enhanced oil recovery system.

4. The apparatus of claim 1 wherein the membrane unit comprises a sheet element comprising edges attached to a ribbed sheet, wherein a membrane envelope is defined between the sheet element and the ribbed sheet.

5. The apparatus of claim 4 wherein the membrane envelope comprises an open edge through which the permeate stream is channeled to the delivery conduit.

6. The apparatus of claim 1 wherein the vacuum-generating device comprises a liquid ring compressor.

7. The apparatus of claim 1 wherein the vacuum-generating device comprises a bellows unit.

8. The apparatus of claim 1 further comprising a secondary enrichment system disposed between the vacuum generating device and the sequestering facility.

9. The apparatus of claim 8 wherein the secondary enrichment system comprises an in-line type enclosed membrane unit.

10. The apparatus of claim 9 wherein the in-line type enclosed membrane unit comprises a sheet membrane element mounted within an enclosed conduit.

11. The apparatus of claim 9 wherein the in-line type enclosed membrane unit comprises a spiral wound membrane element mounted within an enclosed conduit.

12. The system of claim 8 wherein the secondary enrichment system comprises a cryogenic oxygen enrichment system.

13. The system of claim 1 wherein the flue gas generator is pressurized.

14. An apparatus for direct air capture of carbon dioxide from atmospheric air comprising:
   a membrane unit comprising a first membrane sheet, a second membrane sheet, and a ribbed sheet sandwiched between the first membrane sheet and the second membrane sheet, the ribbed sheet comprising a first side comprising a plurality of ribs, the first side in facing relation with a bottom side of the first membrane sheet, wherein an upper envelope is defined between the first side of the ribbed sheet and the bottom side of the first membrane sheet, the first side having a plurality of edges attached to a plurality of corresponding edges of the of the first membrane sheet, the first side further comprising an unattached edge adjacent to a corresponding unattached edge of the first membrane sheet thereby defining an upper envelope open edge, wherein the plurality of ribs on the first side are configured to direct flow to the upper envelope open edge, the ribbed sheet further comprising a second side comprising a plurality of ribs, the second side in facing relation with a top side of the second membrane sheet, wherein a lower envelope is defined between the second side of the ribbed sheet and the top side of the second membrane sheet, the second side having a plurality of edges attached to a plurality of corresponding edges of the second membrane sheet, the second side further comprising an unattached edge adjacent to a corresponding unattached edge of the second membrane sheet thereby defining a lower envelope open edge, wherein the plurality of ribs on the second side are configured to direct flow to the lower envelope open edge;
   a collection conduit having a slot attached to the upper envelope open edge and the lower envelope open edge wherein following the exposure of the first membrane sheet and the second membrane sheet to a gas comprising carbon dioxide, a permeate stream comprising an enriched concentration of carbon dioxide passes into the upper envelope and the lower envelope and passes through the upper envelope open edge and the lower envelope open edge into the collection conduit; and
   a delivery conduit connected to the collection conduit which conducts at least a portion of the enriched concentration of carbon dioxide contained in the permeate stream to a sequestering facility.

15. The apparatus of claim 14 further comprising a vacuum-generating device which applies a vacuum to the membrane unit.

16. A method for direct air capture of components of atmospheric ambient air comprises the following steps:
   exposing a membrane unit to atmospheric air, the membrane unit comprising an outer surface and an inner surface, wherein the membrane unit is configured such that as a first gas comprising a first concentration of oxygen, a first concentration of carbon dioxide and a first concentration of nitrogen is drawn into the outer surface and passes through the membrane unit a permeate stream exits the inner surface where the permeate stream comprises a second concentration of oxygen, a second concentration of carbon dioxide and a second concentration of nitrogen, wherein the second concentration of oxygen is greater than the first concentration of oxygen, the second concentration of carbon dioxide is greater than the first concentration of carbon dioxide, and the second concentration of nitrogen is less than the first concentration of nitrogen;
   applying a vacuum to the membrane unit through a permeate conduit;
   receiving the permeate stream into the permeate conduit;
   utilizing at least a portion of the permeate stream to provide enriched oxygen for a flue gas generator;
   cooling at least a portion of a flue gas stream from the flue gas generator resulting in a produced water condensed from a flue gas stream and a cooled and partially dehydrated flue gas stream;
   delivering at least a portion of the cooled and partially dehydrated flue gas stream to a sequestering facility.

17. The method of claim 16 further comprising the steps of taking the permeate stream from the permeate conduit, transmitting the permeate stream to a secondary enrichment system disposed between the permeate conduit and flue gas generator, which produces a more highly enriched oxygen stream permeate.

18. An apparatus for direct air capture of components of atmospheric air comprising:
   a membrane unit comprising an outer surface and an inner surface, wherein the membrane unit is configured such that as a first gas comprising a first concentration of nitrogen, a first concentration of oxygen, a first concentration of water, and a first concentration of carbon dioxide is drawn into the outer surface and passes through the membrane, a permeate stream exits the inner surface where the permeate stream comprises a second concentration of nitrogen, a second concentration of oxygen, a second concentration of water, and a second concentration of carbon dioxide wherein the second concentration of oxygen is greater than the first concentration of oxygen, the second concentration of water is greater than the first concentration of water, the second concentration of carbon dioxide is greater than the first concentration of carbon dioxide, and the second concentration of nitrogen is less than the first concentration of nitrogen;
   a permeate collection device which collects the permeate stream;
   a vacuum-generating device which applies a vacuum to the membrane unit;
   a secondary enrichment system which receives at least a portion of the permeate stream from the permeate collection device; and a delivery conduit which conducts at least a portion of the permeate stream to a sequestering facility.

* * * * *